United States Patent
Jung et al.

(10) Patent No.: US 8,360,961 B2
(45) Date of Patent: Jan. 29, 2013

(54) CAPSULE-TYPE ENDOSCOPE HAVING SENSOR AND COMMUNICATION METHOD THEREOF

(75) Inventors: Han Jung, Daejeon (KR); Byung-Hyuk Kim, Daejeon (KR); Chul Cha, Daejeon (KR); Yong-Woo Lee, Daejeon (KR)

(73) Assignee: I3System Corp. (KR)

( * ) Notice: Subject to any disclaimer, the term of this patent is extended or adjusted under 35 U.S.C. 154(b) by 631 days.

(21) Appl. No.: 12/595,985

(22) PCT Filed: Jun. 26, 2008

(86) PCT No.: PCT/KR2008/003701
§ 371 (c)(1),
(2), (4) Date: Oct. 15, 2009

(87) PCT Pub. No.: WO2009/011503
PCT Pub. Date: Jan. 22, 2009

(65) Prior Publication Data
US 2010/0137683 A1    Jun. 3, 2010

(30) Foreign Application Priority Data
Jul. 13, 2007    (KR) .................. 10-2007-0070865

(51) Int. Cl.
*A61B 1/04*    (2006.01)

(52) U.S. Cl. ........................................... 600/109
(58) Field of Classification Search ............ 600/109
See application file for complete search history.

(56) References Cited

U.S. PATENT DOCUMENTS

| | | | |
|---|---|---|---|
| 2004/0106849 A1 | 6/2004 | Cho et al. | 600/101 |
| 2004/0171915 A1 | 9/2004 | Glukhovsky et al. | 600/160 |
| 2006/0243288 A1* | 11/2006 | Kim et al. | 128/899 |

FOREIGN PATENT DOCUMENTS

KR    10-2006-0002449    1/2006

OTHER PUBLICATIONS

Written Opinion and International Search Report mailed Jan. 12, 2009 in corresponding PCT International Application No. PCT/KR2008/003701.

* cited by examiner

*Primary Examiner* — Clayton E Laballe
*Assistant Examiner* — Dennis Hancock
(74) *Attorney, Agent, or Firm* — Ostrolenk Faber LLP

(57) ABSTRACT

Disclosed is a capsule-type endoscope, including: a lens for obtaining an image inside the body, one or more sensors for obtaining information related to the inside of the body, a controller for interleaving the information detected by the one or more sensors with the image captured by the lens and encoding the image interleaved with the sensor data for signal output, and a transmitter for transmitting a signal from the controller.

16 Claims, 4 Drawing Sheets

| Image Data (line 1) | Sensor 1 data |
|---|---|
| Image Data (line 2) | Sensor 2 data |
| Image Data (line 3) | Sensor 3 data |
| . | . |
| . | . |
| . | . |
| . | . |
| Image Data (line 210) | Sensor 1 data |
| Image Data (line 211) | Sensor 2 data |
| Image Data (line 212) | Sensor 3 data |
| . | . |
| . | . |
| . | . |
| . | . |

# CAPSULE-TYPE ENDOSCOPE HAVING SENSOR AND COMMUNICATION METHOD THEREOF

CROSS-REFERENCE TO RELATED APPLICATIONS

The present application is a 35 U.S.C. §§371 national phase conversion of PCT/KR2008/003701, filed Jun. 26, 2008, which claims priority of Korean Patent Application No. 10-2007-0070865, filed Jul. 13, 2007. The PCT International Application was published in the English language.

TECHNICAL FIELD

The present invention relates to an endoscope, and more particularly, to a capsule-type endoscope.

BACKGROUND ART

A variety of methods for collecting medical information within a human body have been developed.

In general, an endoscope has been used for a method for collecting image information within the human body. Endoscope captures inside the body and then transmits the captured image to an external device via a communication cable, such as conducting wires and optical fibers. However, if such cable is used in endoscope, even after the endoscope is inserted inside the body, the cable still remains in the mouth (oral cavity), thereby causing a great pain to a patient. In addition, the cable should be manipulated to adjust a region for image capture, thereby causing various side effects, such as damage in the internal organs inside the body, and the like.

In order to solve such problems, Given Imaging Ltd., an Israel-based company has recently developed a capsule-type endoscope, called the "PillCam." If this capsule-type endoscope is swallowed by a patient, similar to a pill, it may transmit image (data) related to the inside of the human body captured by an endoscope camera to an external receiver and thus to implement such image (data) on a monitor.

However, the capsule-type endoscope developed by Given Imaging Ltd., can only capture images, thereby being unsuitable for collecting a variety of information related to the inside of the body. In particular, the capsule-type endoscope developed by Given Imaging Ltd., is very expensive, but information obtained by the endoscope is limited only to the image related to the inside of the body. Accordingly, in order to collect information related to various materials (hormones, or digestive juices) secreted in the internal organs within the body, there is a need to implement another method (or procedure).

DISCLOSURE OF INVENTION

Technical Problem

The present invention is to provide a capsule-type endoscope having various sensors to obtain image information as well as other information.

However, in order to mount the various sensors to the capsule-type endoscope and to transmit information obtained by the sensors to an external entity, there is a need to have a communication module for the sensors, in addition to a communication module for transmitting information obtained from the camera, thereby increasing a volume of the capsule-type endoscope.

Accordingly, another object of the present invention is to reduce the volume of the capsule-type endoscope as well as to transmit information obtained from the sensors to the external entity.

Technical Solution

To achieve these and other advantages and in accordance with an aspect of the present invention, there is provided a capsule-type endoscope, including: a lens for capturing an image inside the body, one or more sensors for obtaining information related to the inside of the body, a controller for interleaving the information obtained by the one or more sensors with the image captured by the lens, encoding the image interleaved with the sensor data, and outputting a signal of the encoded image, and a transmitter for transmitting the signal from the controller.

Here, the one or more sensors can measure a pH (potential of hydrogen), temperature, pressure, vibration, acceleration of the capsule-type endoscope, angular velocity of the capsule-type endoscope, elements of internal secretion or electrical impedance.

The controller may include a sensor data processor for signal-processing and outputting information obtained by the one or more sensors, and an image sensor for receiving a signal from the sensor data processor, interleaving the signal with the image captured by the lens, encoding the interleaved image, and outputting the encoded image.

In addition, the sensor data processor may include a switch for receiving information from the one or more sensors in an alternate manner, and an Analog-to-Digital Converter (ADC) for converting the information from the switch into a digital data, and providing the converted digital data to the image sensor so as to be interleaved with the image captured by the lens.

Further, the image sensor may include a pixel array for capturing an image through the lens and storing the image, a reading unit for sequentially reading a signal for each pixel of the image stored in the pixel array, and an encoding unit for interleaving the signal from the sensor data processor with the signal from the reading unit, encoding the interleaved signal, and outputting the encoded signal.

The transmitter conducts the signal to the body by using electric potential difference through two transmitting electrodes.

To achieve these and other advantages and in accordance with an aspect of the present invention, there is provided a communication method in a capsule-type endoscope, including: obtaining an image inside the body, receiving information related to the inside of the body detected by one or more sensors, interleaving the detected information with the image, encoding the image interleaved with the information, and transmitting the encoded image.

MODE FOR THE INVENTION

Hereinafter, description of the preferred embodiments of present invention is given in detail with reference to the accompanying drawings.

Figure 1:
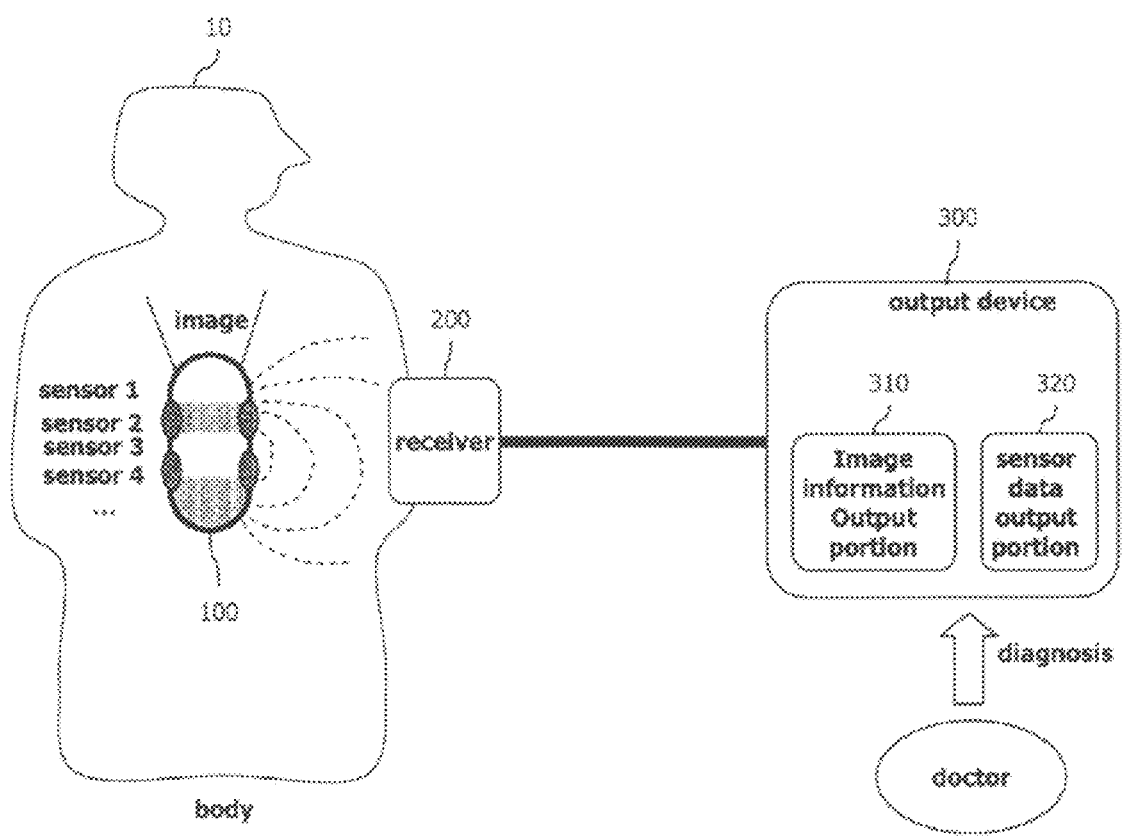
FIG. 1 is a schematic view of a system having a capsule-type endoscope according to the present invention.
Figure 2:
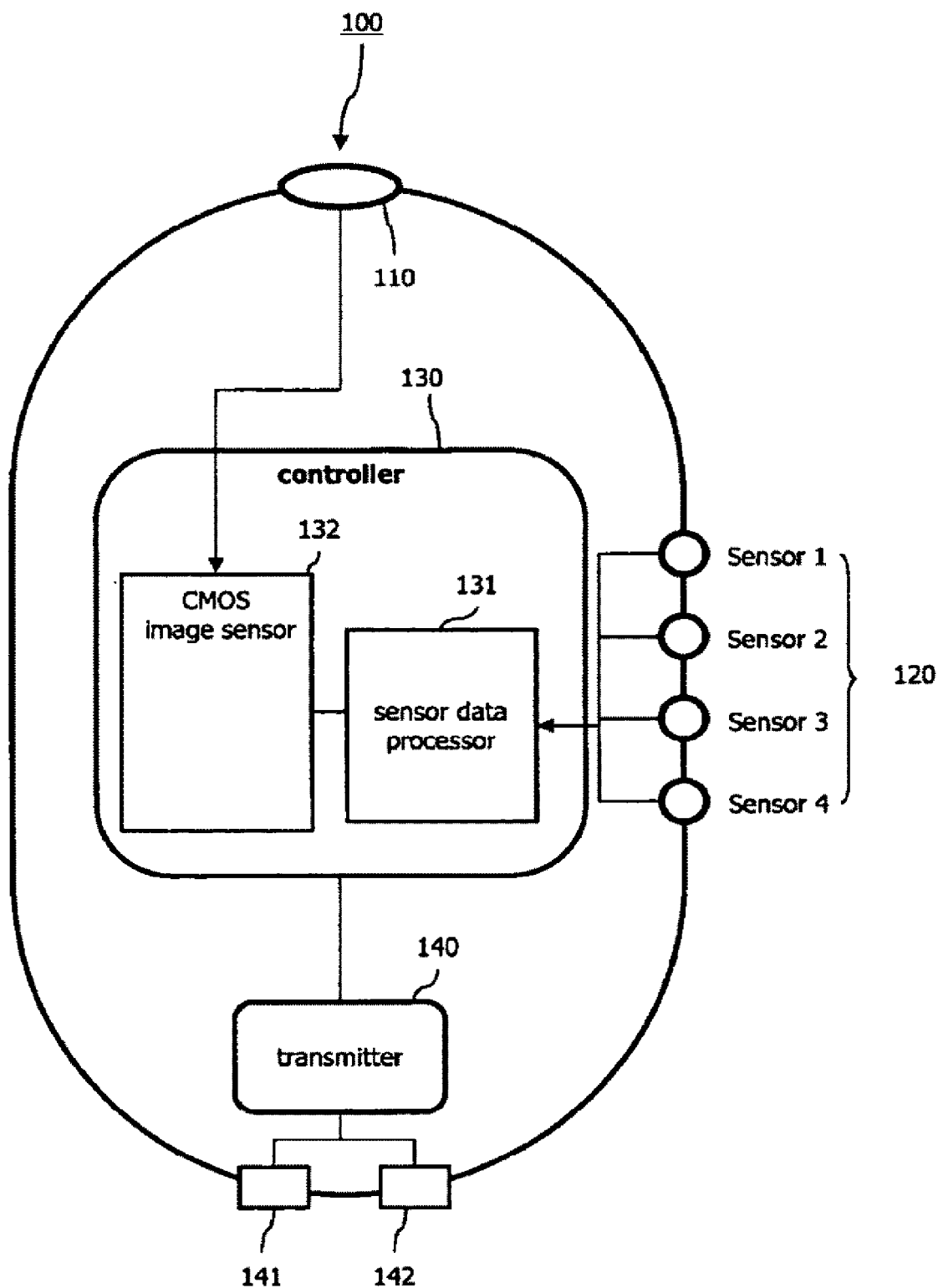
FIG. 2 is a schematic view of the capsule-type endoscope in FIG. 1.
Figure 3:
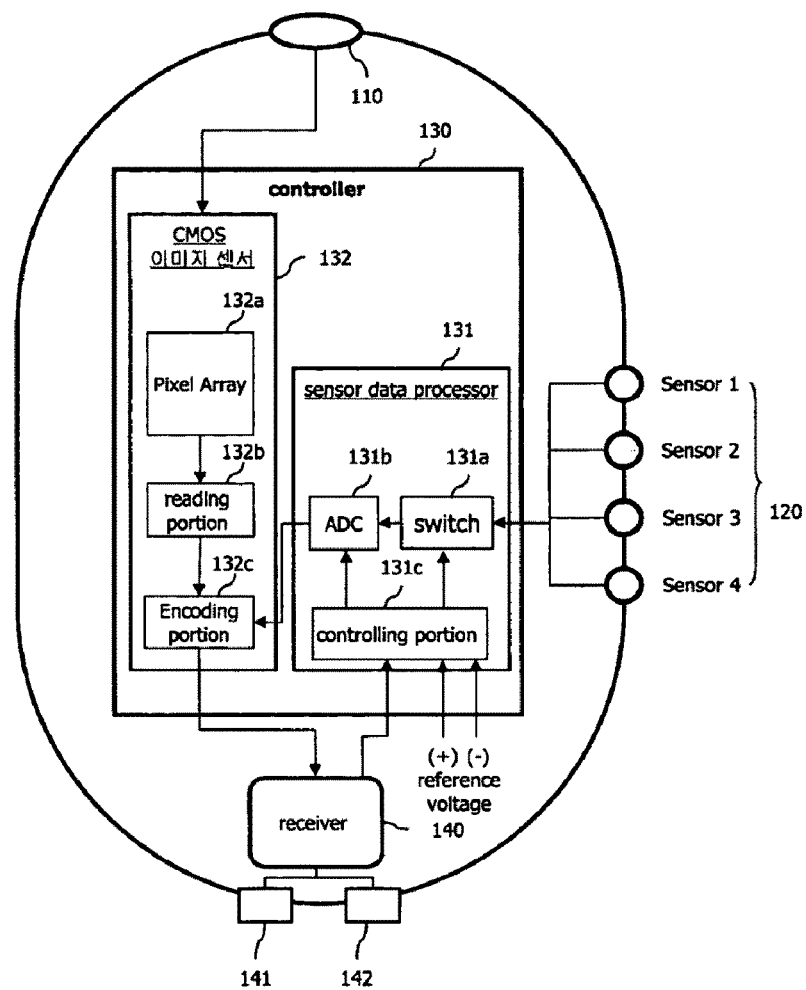
FIG. 3 is a detailed view illustrating the capsule-type endoscope in FIG. 1.

FIG. 1 is a schematic view of a system having a capsule-type endoscope according to the present invention, FIG. 2 is a schematic view of the capsule-type endoscope in FIG. 1, and FIG. 3 is a detailed view illustrating the capsule-type endoscope in FIG. 1.

Referring to FIG. 1, the system according to the present invention may include a capsule-type endoscope 100, a receiver 200, and an output device 300.

The capsule-type endoscope 100, which can be positioned inside the human or animal body 10, e.g., in a digestive organ, is configured to collect a variety of information (e.g., image related to the inside of the body, a pH (potential of hydrogen), temperature or electrical impedance, and the like), and transmit the variety of information via the body 10 to the receiver 200 disposed on a surface of the body 10. Then, the receiver 200 is configured to transfer the received information to the output device 300 which outputs such information.

In more detail, as shown in FIG. 2, the capsule-type endoscope 100 may include a lens 110, one or more sensors 120, a controller 130, and a transmitter (transceiver) 140.

The lens 110 is configured to enable a Complementary Metal Oxide Semiconductor (CMOS) image sensor 132 within the controller 130 to capture an image (a static or dynamic image) of an object disposed inside the human or animal body 10, e.g., inside the digestive organ.

The one or more sensors 120 collect a variety of information (e.g., a pH, temperature, pressure, acceleration, angular velocity (speed), vibration, elements of internal secretion or electrical impedance and the like) and to transmit the collected information to the controller 130.

The controller 130 is configured to encode the image captured via the lens 110, and to interleave information detected by the one or more sensors 120 with the image, thereby outputting such image to the transmitter 140.

More specifically, the controller 130 is provided with a sensor data processor 131 and the CMOS image sensor 132.

The sensor data processor 131 is configured to interleave information detected by the one or more sensors 120 with the image captured via the lens 110. That is, the sensor data processor 131 allows the CMOS image sensor 132 to encode information from the sensors 120 together with the image. Accordingly, a separate transmitter for processing information from the sensors 120 is not required, thereby capable of reducing the volume of the capsule-type endoscope 100. In addition, the sensor data processor 131 may be built within the CMOS image sensor 132, thus to greatly reduce the volume of the capsule-type endoscope 100.

The CMOS image sensor 132 is configured to encode the image of the object captured by the lens 110 and to output the same to the transmitter 140. Here, as above-described, the sensor data processor 131 interleaves the information detected by the sensors 120 with the image.

Referring to FIG. 3, description of the sensor data processor 131 and the CMOS image sensor 132 will be given in detail.

As shown in FIG. 3, the sensor data processor 131 may include a switch 131, an Analog-to-Digital Converter (ADC) 131b, and a controlling portion 131c.

The switch 131a is configured to switch signals received from the one or more sensors 120 and to provide the switched signals to the ADC 131b. That is, the switch 131a provides each signal received from the sensors 120, in an alternate manner, to the ADC 131b.

Having received the signals from each of the sensors 120 through the switch 131a in an alternate manner, the ADC 131b converts the signals into digital signals and forwards the same to the CMOS image sensor 132.

The controlling portion 131c may receive a reference voltage for the ADC 131b inputted from an external entity or generate it by itself, thus to selectively receive the reference voltage according to the external control signal received through the transmitter 140.

The controlling portion 131c may stop an operation of the ADC 131b.

Table 1

TABLE 1

| control signal | reference voltage+ | reference voltage− |
| --- | --- | --- |
| 00 | stop ADC operation | |
| 01 | external input voltage −1 | external input voltage −2 |
| 10 | ⅔ VDD | ⅓ VDD |
| | (VDD: battery voltage) | (VDD: battery voltage) |
| 11 | 1.8 V (fixed) | 0.9 V (fixed) |

That is, as shown in the above table, if the control signal is '00', the operation of the ADC 131b is stopped. If the control signal is '01', the voltage inputted from the outside is used as the reference voltage inputted to the ADC 131b. However, if the control signal is '10', the reference voltage which varies in proportion to the VDD voltage is used. Here, the VDD indicates an external battery voltage. Further, if the control signal is '11', a fixed voltage (e.g., 0.9[V] and 1.8[V]) is provided.

Meanwhile, the CMOS image sensor 132 is further provided with a pixel array 132a, a reading unit 132b and an encoding unit 132c.

The pixel array 132a is configured to capture and store an image signal from the lens 110. The pixel array 132a is configured to have 324*324 pixels so as to capture an image signal of a high-resolution.

The reading unit 132b is configured to sequentially read signals of each pixel, and the encoding unit 132c is configured to encode the signal from the reading unit 132b and to output the same to the transmitter 140.

Meanwhile, the transmitter 140 converts the encoded signal into an electric signal, and then applies the converted signal to two transmitting electrodes 141, 142 through an output line.

The transmitting electrodes 141, 142 are configured to contact the inside of the body 10, such that electric potential difference between the two transmitting electrodes is generated according to data to be transmitted, thus to enable a conduction current to flow in the body 10. The current starting from the transmitting electrode of a high electric potential flows to the transmitting electrode of a low electric potential through a certain path within the body 10. Here, a portion of the current flowing in the body may also reach the surface of the body, thus to enable receiving electrodes of the receiver 200 mounted on the surface of the body to induce a certain level of a voltage from the current having reached the surface of the body.

The receiver 200 receives a signal from the capsule-type endoscope 100 and transmits the same to the output device 300. Here, the receiver 200 may store the signal for a certain period of time, since the receiver 200, as shown in the drawing, is attached to the human or animal body. Accordingly, the human or animal may undergo endoscopy and an examination for an internal secretion while carrying out his normal activities for several hours, without being present at a hospital.

The output device 300 decodes the signal received from the receiver 200, separates the sensor data from the image, and then outputs the same respectively to an image information output portion 310 and a sensor data output portion 320 as shown in FIG. 1.

Figure 4:
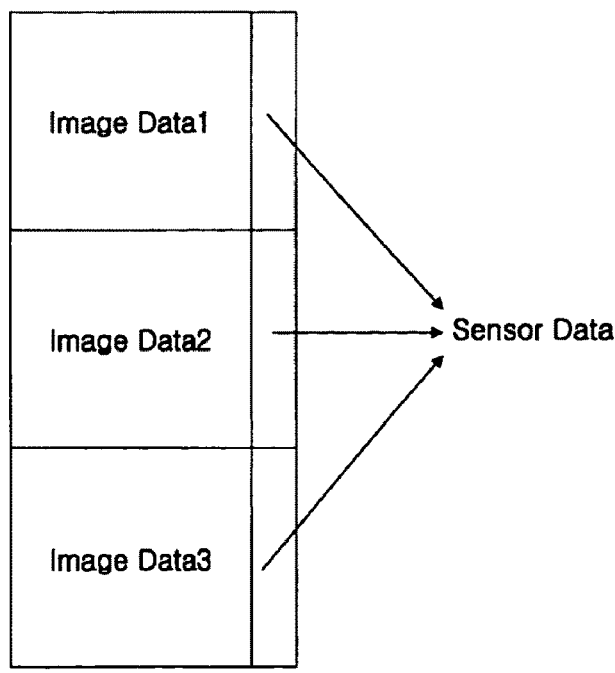
FIG. 4 is an exemplary view illustrating the structure of data encoded in the capsule-type endoscope in FIG. 1 in a frame unit.
Figures 5, 6:
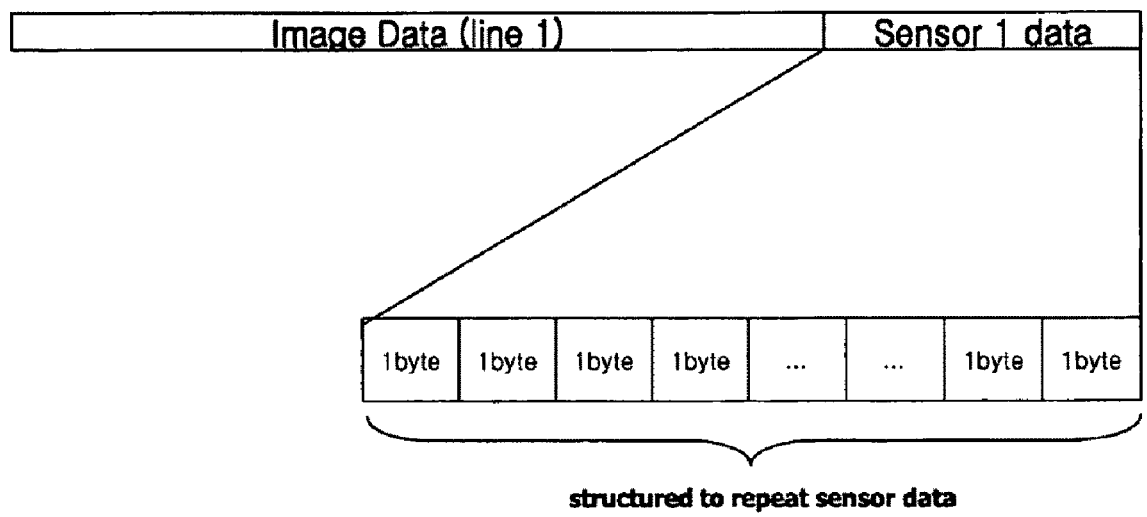
FIG. 5 is an exemplary view illustrating the structure of data encoded in the capsule-type endoscope in FIG. 1 in a line unit.
FIG. 6 is an exemplary view illustrating more detailed structure in the line unit in FIG. 5.

FIG. 4 is an exemplary view illustrating the structure of data encoded in the capsule-type endoscope in FIG. 1 in a frame unit, FIG. 5 is an exemplary view illustrating the structure of data encoded in the capsule-type endoscope in FIG. 1 in a line unit, and FIG. 6 is a detailed view illustrating the structure in the line unit in FIG. 5.

Referring to FIG. 4, data from the one or more sensors 120 is inserted into each frame of the image. Here, the data from the sensors 120 may be inserted into an end portion of each image.

Referring to FIG. 5, data from the one or more sensors 120 is inserted into each line within a frame. That is, data from a first sensor among the one or more sensors 120 is configured to be inserted into a first line of the image, and data from a second sensor is configured to be inserted into a second line of the image.

Meanwhile, the one or more sensors 120 are operated in a high rate, thus allowing data detected by the one or more sensors 120 several times to be inserted into the frame. For instance, if it is assumed that 4 sensors are provided, data firstly detected by the 4 sensors can be inserted into the first through fourth lines of the frame, and data secondly detected by the 4 sensors can be inserted into the fifth through eighth lines of the frame.

Referring to FIG. 6, data detected by the sensors 120 may be repeated in each line of the image. This is to prevent an occurrence of an error in the data due to an impact, such as external noise and the like. FIG. 5 shows that the sensor data is construed in 1 byte and 1 byte data is repeated.

As so far described, the present invention mounts one or more sensors to the capsule-type endoscope, thereby obtaining a great amount of information at one time and reducing the cost for an operator.

The present invention interleaves information detected by the one or more sensors with the image captured by the lens, encodes the image interleaved with the sensor data, and then outputs a signal of the encoded image, thereby not requiring a separate communication module only for the sensors. In addition, the volume of the capsule-type endoscope as well as a manufacturing cost be reduced.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

The invention claimed is:

1. A capsule-type endoscope, comprising:
a lens for capturing an image inside the body;
a plurality of sensors for obtaining information related to the inside of the body;
a controller for interleaving the information obtained by the plurality of sensors with the image captured by the lens, which is interleaved with the sensor data, and outputting a signal of the encoded image,
wherein the endoscope is configured to interleave the information into each frame of the image or each line of the image;
a transmitter for transmitting a signal from the controller; and
a switch for receiving information from the plurality of sensors in an alternate manner.

2. The capsule-type endoscope of claim 1, wherein the plurality of sensors are to measure at least one of a pH (potential of hydrogen), temperature, pressure, vibration, acceleration of the capsule-type endoscope, angular velocity of the capsule-type endoscope, elements of internal secretion or electrical impedance.

3. The capsule-type endoscope of claim 1, wherein the controller comprises:
a sensor data processor for signal-processing an outputting information obtained by the plurality of sensors; and
an image sensor for receiving a signal from the sensor data processor, interleaving the signal with the image captured by the lens, encoding the image with which the signal is interleaved, and outputting the encoded image.

4. The capsule-type endoscope of claim 3, wherein the sensor data processor comprises:
the switch for receiving information from the plurality of sensors in an alternate manner; and
an Analog-to-Digital Converter (ADC) for converting the information from the switch into a digital data, and providing the converted digital data to the image sensor so as to be interleaved with the image captured by the lens.

5. The capsule-type endoscope of claim 4, wherein the controller controls a reference voltage applied to the ADC according to an external control signal.

6. The capsule-type endoscope of claim 3, wherein the image sensor comprises:
a pixel array for capturing an image through the lens and storing the captured image;
a reading unit for sequentially reading a signal for each pixel of the image stored in the pixel array; and
an encoding unit for interleaving the signal from the sensor data processor with the signal from the reading unit, encoding the interleaved signal, and outputting the encoded signal.

7. The capsule-type endoscope of claim 1, wherein the transmitter conducts the signal to the body by using electric potential difference through two transmitting electrodes.

8. The capsule-type endoscope of claim 1, wherein one frame of the encoded image includes both captured image information and non-image information.

9. A capsule-type endoscope, comprising:
a lens for capturing an image inside the body;
a plurality of sensors for obtaining information related to the inside of the body;
a sensor data processor for signal-processing an outputting information obtained by the plurality of sensors,
wherein the sensor data processor comprises a switch for receiving information from the plurality of sensors in an alternate manner;
an image sensor for receiving a signal from the sensor data processor, interleaving the signal with the image captured by the lens, encoding the interleaved image, and outputting a signal of the encoded image;
wherein the endoscope is configured to interleave the information into each frame of the image or each line of the image; and
a transmitter for transmitting the signal from the image sensor.

10. The capsule-type endoscope of claim 9, wherein the transmitter conducts the signal to the body by using electric potential difference through two transmitting electrodes.

11. The capsule-type endoscope of claim 9, wherein the sensor data processor further comprises:
an Analog-to-Digital Converter (ADC) for converting the information from the switch into a digital data, and providing the converted digital data to the image sensor so as to be interleaved with the image captured by the lens.

12. The capsule-type endoscope of claim 9, wherein one frame of the encoded image includes both captured image information and non-image information.

13. A communication method in a capsule-type endoscope, comprising:
capturing an image inside the body;
receiving information related to the inside of the body detected by a plurality of sensors;
switching the received information from the plurality of sensors in an alternate manner;
interleaving the detected information with the image,
wherein the detected information is interleaved into each frame of the image or each line of the image;
encoding the image interleaved with the information; and
transmitting the encoded image.

14. The communication method of claim 13, wherein the information detected by the plurality of sensors include at least one or more of a pH (potential of hydrogen), temperature, pressure, vibration, acceleration of the capsule-type endoscope, angular velocity of the capsule-type endoscope, elements of internal secretion or electrical impedance.

15. The communication method of claim 13, wherein the step of transmitting is conducting the signal of the image to the body by using electric potential difference through two transmitting electrodes.

16. The communication method of claim 13, wherein one frame of the encoded image includes both captured image information and non-image information.

* * * * *